(12) United States Patent
Koo et al.

(10) Patent No.: US 11,345,981 B2
(45) Date of Patent: May 31, 2022

(54) BIODEGRADABLE METAL ALLOY WITH MULTIPLE PROPERTIES

(71) Applicant: U & I CORPORATION, Gyeonggi-do (KR)

(72) Inventors: Ja Kyo Koo, Gyeonggi-do (KR); Hwa Chul Jung, Seoul (KR); Won Hyun Shim, Gyeonggi-do (KR); Hyung Jin Roh, Gyeonggi-do (KR); Hyun Kwang Seok, Seoul (KR); Yu Chan Kim, Gyeonggi-do (KR)

(73) Assignee: U & I CORPORATION, Gyeonggi-do (KR)

( * ) Notice: Subject to any disclaimer, the term of this patent is extended or adjusted under 35 U.S.C. 154(b) by 0 days.

(21) Appl. No.: 16/226,873

(22) Filed: Dec. 20, 2018

(65) Prior Publication Data
US 2020/0173000 A1 Jun. 4, 2020

(30) Foreign Application Priority Data

Nov. 30, 2018 (KR) .................. 10-2018-0152118

(51) Int. Cl.
| | | |
|---|---|---|
| C22C 23/04 | (2006.01) | |
| C22C 23/06 | (2006.01) | |
| C22F 1/06 | (2006.01) | |
| A61L 27/04 | (2006.01) | |
| C22C 1/02 | (2006.01) | |
| A61L 31/02 | (2006.01) | |

(52) U.S. Cl.
CPC .............. *C22C 23/04* (2013.01); *C22C 23/06* (2013.01); *C22F 1/06* (2013.01); *A61L 27/047* (2013.01); *A61L 31/022* (2013.01); *C22C 1/02* (2013.01); *C22C 2200/00* (2013.01); *C22C 2202/00* (2013.01)

(58) Field of Classification Search
CPC ........... C22C 23/04; C22C 23/06; C22C 1/02; C22C 2200/00; C22C 2202/00; C22F 1/06; A61L 27/047; A61L 31/022
See application file for complete search history.

(56) References Cited

U.S. PATENT DOCUMENTS 8,293,031 B2 * 10/2012 Gerold .................... C22C 23/00
148/420

FOREIGN PATENT DOCUMENTS

KR  10-2014-0099431    8/2014

OTHER PUBLICATIONS

Mukai et al ("Fabrication of a magnesium alloy with excellent ductility for biodegradable clips", Acta Biomaterialia 29 (2016) 468-476) (Year: 2016).*

* cited by examiner

Primary Examiner — Robert S Jones, Jr.
Assistant Examiner — Jiangtian Xu

(57) ABSTRACT

The present disclosure relates to a biodegradable metal alloy with multiple properties, containing: 0.05-0.15 wt % of calcium; a metal element X having a HCP structure, of a composition not forming a precipitated phase when mixed with magnesium; and magnesium as the remainder.

6 Claims, 1 Drawing Sheet

Mixing metal element X having HCP structure, of composition not forming precipitated phase when mixed with magnesium, Ca and Mg Extruding molten alloy through at least two sintering processes Mixing metal element X having HCP structure, of composition not forming precipitated phase when mixed with magnesium, Ca and Mg
Extruding molten alloy through at least two sintering processes

BIODEGRADABLE METAL ALLOY WITH MULTIPLE PROPERTIES

CROSS-REFERENCE TO RELATED APPLICATION

This application claims priority of Korean Patent Application No. 10-2018-0152118, filed on Nov. 30, 2018, in the KIPO (Korean Intellectual Property Office), the disclosure of which is incorporated herein entirely by reference.

BACKGROUND OF THE INVENTION

Field of the Invention

The present disclosure relates to a biodegradable metal alloy with multiple properties, more particularly to a biodegradable metal alloy with multiple properties, which exhibits improved corrosiveness and strength as well as elongation and toughness by adding a dissimilar metal element to a magnesium alloy.

Description of the Related Art

Recently, metals that are degraded in the body are being studied as implant and stent materials used for medical purposes.

The biodegradable metals should have superior mechanical properties to endure the torsional stress generated from a screw or the load generated from bone fracture when implanted in the body. Among them, toughness refers to the amount of energy capable of absorbing the torsional stress generated from the screw or the load generated from bone fracture, etc. In general, to improve the toughness, the improvement of yield point and elongation is necessary. For this, it is required to refine the metal alloy texture through additional processes such as quenching, sintering, heat treatment, etc. of the biodegradable metal and control the internal residual stress. In addition, the metal alloy used as a biodegradable metal should be designed appropriately in terms of added elements and alloy composition. The alloy composition is changed generally with the amount of elements added. The mechanical strength is improved as the amount of elements added to the alloy is increased.

However, the increase in the amount of the added elements leads to generation of metal-metal compounds or secondary phases, which causes the formation of a microgalvanic circuit that accelerates corrosion. This increases the corrosion rate of the biodegradable metal. In addition, the elements added to the biodegradable metal may accelerate or decelerate the degradation of the biodegradable metal alloy by preventing or promoting galvanic corrosion. Accordingly, a biodegradable metal material which merely exhibits good mechanical properties and fast biodegradation rate cannot be applied to implants.

In this regard, Korean Patent Publication No. 10-2014-0099431 discloses a biodegradable implant containing magnesium, which contains, as impurities, manganese (Mn) and at least one selected from a group consisting of iron (Fe), nickel (Ni) and a mixture of iron (Fe) and nickel (Ni), wherein the content of the impurities is more than 0 and less than or equal to 1 part by weight based on 100 parts by weight of the magnesium and the ratio of {at least one selected from a group consisting of iron (Fe), nickel (Ni) and a mixture of iron (Fe) and nickel (Ni)}/manganese (Mn) is greater than 0 and smaller than or equal to 5, and a method for manufacturing the same.

However, the technology of ensuring satisfactory mechanical properties, particularly toughness, in consideration of elongation and strength while decreasing corrosion rate is still not enough.

SUMMARY OF THE INVENTION

The present disclosure is directed to providing a biodegradable metal alloy based on a new composition, which has improved corrosiveness and mechanical properties, and a method for preparing the same.

The present disclosure provides a biodegradable metal alloy with multiple properties, which contains: 0.05-0.15 wt % of calcium; a metal element X having a HCP structure, of a composition not forming a precipitated phase when mixed with magnesium; and magnesium as the remainder.

In an exemplary embodiment of the present disclosure, the X is at least one selected from a group consisting of Sc, Gd, Dy, Y, Nd, Ho, Er, Tm, Lu and Zn.

In an exemplary embodiment of the present disclosure, the solid solubility of the X for magnesium is 5% or higher and the content of the X based on the total biodegradable metal alloy is 0.1 wt % or greater and less than 2 wt %.

In an exemplary embodiment of the present disclosure, the biodegradable metal alloy with multiple properties is extruded after casting and the biodegradable metal alloy with multiple properties has a toughness of 5000 or higher.

In an exemplary embodiment of the present disclosure, the biodegradable metal alloy with multiple properties has a corrosion rate of 0.005 $mL/cm^2/hr$ or lower in a phosphate-buffered saline (PBS) which simulates the in-vivo environment.

According to the present disclosure, by adding an element with a HCP structure, having high solid solubility for magnesium, and calcium together to magnesium, thereby improving mechanical properties (strength and elongation) and toughness, the resistance to torsional stress, load carrying capacity at the fracture site and corrosiveness can be improved at the same time when the metal alloy is used as a biodegradable implant. Accordingly, the biodegradable metal alloy may be used as a material for a biodegradable implant such as an implant for bone or ligament reinforcement, a stent, etc.

BRIEF DESCRIPTION OF THE DRAWINGS

The above and other features and advantages will become more apparent to those of ordinary skill in the art by describing in detail exemplary embodiments with reference to the attached drawings, in which:

FIG. 1 shows a flow diagram of a method for preparing a high-elongation magnesium alloy according to an exemplary embodiment of the present disclosure.

In the following description, the same or similar elements are labeled with the same or similar reference numbers.

DETAILED DESCRIPTION

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", "comprises" and/or "comprising," when used in this specification, specify the presence of stated features, integers, steps, operations, elements, and/or components, but do not preclude the presence or addition of one or more other features, integers, steps, operations, elements, components, and/or groups thereof. In addition, a term such as a "unit", a "module", a "block" or like, when used in the specification, represents a unit that processes at least one function or operation, and the unit or the like may be implemented by hardware or software or a combination of hardware and software.

Reference herein to a layer formed "on" a substrate or other layer refers to a layer formed directly on top of the substrate or other layer or to an intermediate layer or intermediate layers formed on the substrate or other layer. It will also be understood by those skilled in the art that structures or shapes that are "adjacent" to other structures or shapes may have portions that overlap or are disposed below the adjacent features.

In this specification, the relative terms, such as "below", "above", "upper", "lower", "horizontal", and "vertical", may be used to describe the relationship of one component, layer, or region to another component, layer, or region, as shown in the accompanying drawings. It is to be understood that these terms are intended to encompass not only the directions indicated in the figures, but also the other directions of the elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Preferred embodiments will now be described more fully hereinafter with reference to the accompanying drawings. However, they may be embodied in different forms and should not be construed as limited to the embodiments set forth herein. Rather, these embodiments are provided so that this disclosure will be thorough and complete, and will fully convey the scope of the disclosure to those skilled in the art.

The inventors of the present disclosure have developed an alloy with high toughness by adding magnesium, calcium and an element having the same HCP (hexagonal close-packing) structure as magnesium, thereby improving strength and elongation.

In particular, the present disclosure can provide improved strength and elongation by adding an alloying element with a HCP structure, which has a high solid solubility for magnesium, and adding a trace amount of calcium element, thereby refining crystal grains.

But, when an element with a HPC structure, which has low solid solubility (lower than 5% for magnesium), is used, metal-metal compounds and precipitated phases may be formed easily. The precipitated phase acts as a cause of increasing corrosion rate in the in-vivo environment by forming a galvanic circuit. The added calcium element may improve mechanical properties by refining the crystal grain size. But, if it is added in an excessive amount, precipitated phases such as $Mg_2Ca$, etc. are formed excessively, resulting in increased corrosion rate. Accordingly, by designing an appropriate composition of an element having high solid solubility for magnesium and having a HCP structure (not forming a precipitated phase) and the Ca element, a biodegradable magnesium alloy with superior mechanical properties and corrosiveness may be provided.

A biodegradable metal alloy according to an exemplary embodiment of the present disclosure contains: 0.05-0.15 wt % of calcium based on magnesium; and a metal element X having a HCP structure, of a composition not forming a precipitated phase when mixed with magnesium. In the present disclosure, the X may be at least one selected from a group consisting of Sc, Gd, Dy, Y, Nd, Ho, Er, Tm, Lu and Zn, as an element having a solid solubility of 5 wt % or higher for magnesium.

In the present disclosure, the element having a HCP structure is used to decrease corrosion rate in vivo and to improve mechanical properties such as elongation, etc.

In an exemplary embodiment of the present disclosure, the content of the X is 0.1-1.5 wt % based on the total biodegradable metal alloy. If the content is below the lower limit, the actual effect of improving corrosiveness may be insignificant and superior mechanical properties may not be achieved. And, if it exceeds the upper limit, mechanical properties are improved but a large amount of hydrogen gas may be generated because of too high degradation rate.

Hereinafter, the present disclosure is described in more detail through specific examples.

EXAMPLES

A magnesium ingot prepared using a stainless steel (SUS410) crucible was loaded in a crucible. The magnesium-loaded crucible was heated. When the temperature of the molten magnesium reached 700° C. or higher, zinc (Zn) and calcium (Ca) were loaded and the molten mixture of calcium, zinc and magnesium in the crucible was stirred to be mixed well with each other. The completely molten magnesium alloy was poured into a mold having a diameter of 50 mm and then water-cooled to refine the magnesium alloy texture.

Then, after surface-processing the cast magnesium alloy in solid state, direct extrusion was performed. In an example of the present disclosure, the extrusion speed was set to 0.1-0.3 mm/sec and the reduction in cross-sectional area before and after the extrusion (extrusion ratio) was set to 39:1.

The mechanical properties of biodegradable magnesium implant samples prepared as described above with the compositions described in Table 1 were evaluated according to ASTM-B557M-15. The result is summarized in Table 1.

TABLE 1

|  | Mg alloy | UTS (MPa) | S.D (MPa) | Elongation (%) | S.D (%) | Yield strength (MPa) | Toughness |
|---|---|---|---|---|---|---|---|
| Comparative Example 1 | Pure Mg | 184.2 | 8.1 | 17.2 | 0.7 | 118.1 | 3250 |
| Comparative Example 2 | Mg—1Zn | 222.4 | 12.1 | 17.8 | 1.3 | 106.7 | 3773 |

TABLE 1-continued

| Mg alloy | | UTS (MPa) | S.D (MPa) | Elongation (%) | S.D (%) | Yield strength (MPa) | Toughness |
|---|---|---|---|---|---|---|---|
| Comparative Example 3 | Mg—2Zn—0.1Ca | 242.7 | 2 | 25.3 | 1.4 | 148.6 | 5303 |
| Comparative Example 4 | Mg—3Zn—0.1Ca | 247.4 | 3.4 | 25.2 | 1.5 | 131.4 | 5232 |
| Comparative Example 5 | Mg—1Ca(FCC) | 229.2 | 7.9 | 13.3 | 4.7 | 186.8 | 1846 |
| Comparative Example 6 | Mg—5Ca—1Zn | 278.2 | 3.5 | 8.2 | 2.3 | 251.2 | 1656 |
| Example 1 | Mg—1Zn—0.1Ca | 230.3 | 4.1 | 30.1 | 2.9 | 206.4 | 7584 |
| Example 2 | Mg—1Sc—0.1Ca | 197.6 | 4.4 | 29.6 | 3.1 | 161.8 | 5667 |
| Example 3 | Mg—1Dy—0.1Ca | 193.4 | 3.2 | 30.3 | 1.9 | 148.8 | 5677 |
| Example 4 | Mg—1Gd—0.1Ca | 208.6 | 3.6 | 30.5 | 3.0 | 166.4 | 6019 |
| Example 5 | Mg—1Y—0.1Ca | 198 | 0.3 | 27.8 | 2.1 | 155.7 | 5640 |

As shown in Table 1, the elongation was improved remarkably when an element with a HCP structure having a solid solubility for magnesium of 5 wt % or higher and 0.1 wt % of calcium were added. However, when zinc with a HCP structure was added in excess amounts (Comparative Examples 3 and 4), corrosiveness was increased rapidly as shown in Table 2. Accordingly, the adequate content of the HCP metal element in terms of the improvement of mechanical properties and in-vivo corrosiveness is 0.1-2 wt %.

Regarding toughness, as compared to the commercially available biodegradable magnesium alloy containing 5 wt % of zinc and 1 wt % of calcium (Comparative Example 6), Examples 1-5 within the composition ranges of the present disclosure showed about 4 times higher toughness. This is due to the combination of the HCP element and Ca at the given composition ranges. In addition, the improvement in corrosiveness can be expected as shown in Table 2.

Table 2 shows a result of comparative analysis of in-vivo corrosiveness.

TABLE 2

| | | $H_2$ gas generation rate (ml/cm²/hrs) | | | |
|---|---|---|---|---|---|
| | Mg alloy | Averg. (48 hrs) | S.D | Averg. (168 hrs) | S.D |
| Comparative Example 1 | Pure Mg | 0.010 | 0.001 | 0.006 | 0.001 |
| Comparative Example 3 | Mg—2Zn—0.1Ca | 0.014 | 0.001 | 0.009 | 0.003 |
| Comparative Example 4 | Mg—3Zn—0.1Ca | 0.023 | 0.007 | 0.031 | 0.014 |
| Comparative Example 5 | Mg—1Ca(FCC) | 0.062 | 0.011 | 0.133 | 0.017 |
| Comparative Example 6 | Mg—5Ca—1Zn | 0.016 | 0.005 | 0.010 | 0.020 |
| Example 1 | Mg—1Zn—0.1Ca | 0.005 | 0.001 | 0.004 | 0.001 |
| Example 2 | Mg—1Sc—0.1Ca | 0.010 | 0.001 | 0.005 | 0.001 |
| Example 3 | Mg—1Dy—0.1Ca | 0.010 | 0.001 | 0.005 | 0.000 |
| Example 4 | Mg—1Gd—0.1Ca | 0.009 | 0.001 | 0.004 | 0.001 |
| Example 5 | Mg—1Y—0.1Ca | 0.009 | 0.001 | 0.005 | 0.001 |

Referring to Table 2, it can be seen that the corrosion rate in a phosphate-buffered saline (PBS) which simulates the in-vivo environment decreases greatly when 0.15 wt % of calcium and 1 wt % of the HCP element X were added (hydrogen generation is proportional to the corrosion rate).

When compared with the commercially available biodegradable magnesium alloy material (Comparative Example 6), those of the examples showed about 2 times superior corrosion resistance at 168 hours. In addition, when the content of X was increased to 2-3 wt % (Comparative Examples 3 and 4), the strength was improved but the corrosion rate was increased. It seems that the corrosion rate was increased because zinc or calcium was not completely dissolved and precipitated phases such as $Mg_2Ca$ or $Ca_2Mg_6Zn_3$ were formed.

From the above results, it can be seen that an alloy with improved mechanical properties and good corrosion resistance can be prepared by adding less than 0.15 wt % of calcium and 0.1-1.5 wt % of the element X having a HCP structure (X=Sc, Gd, Dy, Y, Nd, Ho, Er, Tm, Lu or Zn) to Mg.

In particular, the present disclosure enables the preparation of a biodegradable magnesium alloy with the change in elongation being 15% or greater and having a strength-ductility index of 7000 MPa % or higher without change in corrosion rate by controlling only the crystal grain size.

Moreover, in the present disclosure, the crystal grain size is controlled through a multi-step extrusion process (250-380° C.). For this, the element X having a HCP structure and Ca are molten with Mg.

FIG. 1 shows a flow diagram of a method for preparing a high-elongation magnesium alloy according to an exemplary embodiment of the present disclosure.

Referring to FIG. 1, the method for preparing a high-elongation magnesium alloy according to an exemplary embodiment of the present disclosure includes: a step of mixing a metal element X having a HCP structure, of a composition not forming a precipitated phase when mixed with magnesium, Ca and Mg; and a step of extruding the molten alloy through at least two sintering processes.

In particular, the present disclosure can provide improved strength and elongation by adding an alloying element with a HCP structure, which has a high solid solubility for magnesium, and adding a trace amount of calcium element, thereby refining crystal grains.

But, when an element with a HPC structure, which has low solid solubility (lower than 5% for magnesium), is used, metal-metal compounds and precipitated phases may be formed easily. The precipitated phase acts as a cause of increasing corrosion rate in the in-vivo environment by forming a galvanic circuit. The added calcium element may improve mechanical properties by refining the crystal grain size. But, if it is added in an excessive amount, precipitated phases such as $Mg_2Ca$, etc. are formed excessively, resulting in increased corrosion rate. Accordingly, by designing an appropriate composition of an element having high solid solubility for magnesium and having a HCP structure (not forming a precipitated phase) and the Ca element, a biodegradable magnesium alloy with superior mechanical properties and corrosiveness may be provided.

A biodegradable metal alloy according to an exemplary embodiment of the present disclosure contains: 0.05-0.15 wt % of calcium based on magnesium; and a metal element X having a HCP structure, of a composition not forming a precipitated phase when mixed with magnesium. In the present disclosure, the X may be at least one selected from a group consisting of Sc, Gd, Dy, Y, Nd, Ho, Er, Tm, Lu and Zn, as an element having a solid solubility of 5 wt % or higher for magnesium.

In the present disclosure, the element having a HCP structure is used to decrease corrosion rate in vivo and to improve mechanical properties such as elongation, etc.

In an exemplary embodiment of the present disclosure, the content of the X is 0.1-1.5 wt % based on the total biodegradable metal alloy. If the content is below the lower limit, the actual effect of improving corrosiveness may be insignificant and superior mechanical properties may not be achieved. And, if it exceeds the upper limit, mechanical properties are improved but a large amount of hydrogen gas may be generated because of too high degradation rate.

While the present disclosure has been described with reference to the embodiments illustrated in the figures, the embodiments are merely examples, and it will be understood by those skilled in the art that various changes in form and other embodiments equivalent thereto can be performed. Therefore, the technical scope of the disclosure is defined by the technical idea of the appended claims The drawings and the forgoing description gave examples of the present invention. The scope of the present invention, however, is by no means limited by these specific examples. Numerous variations, whether explicitly given in the specification or not, such as differences in structure, dimension, and use of material, are possible. The scope of the invention is at least as broad as given by the following claims.

What is claimed is:

1. A biodegradable metal alloy, consisting of:
   0.05-0.15 wt % of calcium;
   a metal element X within an HCP structure, of a composition not forming a precipitated phase when mixed with magnesium; and
   magnesium as the remainder,
   wherein the X is Zn,
   wherein the solid solubility of the X for magnesium is 5% or higher,
   wherein the X is 1 wt % or greater and less than 2 wt %.

2. The biodegradable metal alloy of claim 1, wherein the biodegradable metal alloy is extruded after casting.

3. The biodegradable metal alloy of claim 2, wherein the biodegradable metal alloy has a corrosion rate of 0.005 mL/cm$^2$/hr or lower in a phosphate-buffered saline (PBS) which simulates the in-vivo environment.

4. A biodegradable metal alloy, consisting of:
   0.05-0.15 wt % of calcium;
   1-2 wt % of a metal element X within an HCP structure, of a composition not forming a precipitated phase when mixed with magnesium; and
   99.85-97.85 wt % of magnesium,
   wherein the X is Zn,
   wherein the solid solubility of the X for magnesium is 5% or higher.

5. The biodegradable metal alloy of claim 4, wherein the biodegradable metal alloy is extruded after casting.

6. The biodegradable metal alloy of claim 4, wherein the biodegradable metal alloy has a corrosion rate of 0.005 mL/cm2/hr or lower in a phosphate-buffered saline (PBS) which simulates the in-vivo environment.

* * * * *